United States Patent [19]

Müller et al.

[11] Patent Number: 5,130,406
[45] Date of Patent: Jul. 14, 1992

[54] INITIATORS FOR MATERIALS WHICH CAN BE POLYMERIZED CATIONICALLY

[75] Inventors: Beat Müller, Marly; Dieter Baumann, Möhlin, both of Switzerland

[73] Assignee: Ciba-Geigy Corporation, Ardsley, N.Y.

[21] Appl. No.: 496,557

[22] Filed: Mar. 19, 1990

[30] Foreign Application Priority Data

Mar. 21, 1989 [CH] Switzerland .................. 1037/89

[51] Int. Cl.$^5$ .................. C07F 15/02; C08G 59/68
[52] U.S. Cl. .................. 528/92; 528/357; 528/358; 528/361; 528/366; 528/55; 528/56; 528/57; 528/58; 528/371; 252/182.2; 252/182.28; 252/182.23
[58] Field of Search .................. 528/92, 357, 358, 361, 528/366, 55, 56, 57, 58, 371; 252/182.2, 182.28, 182.23

[56] References Cited

U.S. PATENT DOCUMENTS

| 3,585,227 | 6/1971 | Dreyfuss | 260/440 |
| 4,321,351 | 3/1982 | Zuppinger et al. | 528/91 |
| 4,726,185 | 12/1987 | Rabener et al. | 528/92 |
| 4,756,787 | 7/1988 | Drain et al. | 528/92 |

FOREIGN PATENT DOCUMENTS

| 0094915 | 2/1984 | European Pat. Off. . |
| 0109815 | 5/1984 | European Pat. Off. . |
| 0235077 | 9/1987 | European Pat. Off. . |

OTHER PUBLICATIONS

Angew. Chem. 97, pp. 879–880, (1985).
J. Chem. Soc. Chem. Comm., (1976) pp. 33–34.
J. Chem. Soc. Dalton Trans. 1987, p. 2379.
Angew. Chem. 96(5), pp. 357–358 (1984).
Macromolecules 21, 1916–1920 (1988).
Inorganica Chimica Acta, 33, 261–264 (1979).
J. Am. Chem. Sec. 104, 5586–6694 (1982).

*Primary Examiner*—John C. Bleutge
*Assistant Examiner*—Frederick Krass
*Attorney, Agent, or Firm*—JoAnn Villamizar

[57] ABSTRACT

Initiator compositions for materials which can be polymerized cationically are described, these containing i) an anhydride of a polycarboxylic acid, a polyisocyanate, a cyclic carbonate, a lactone or a mixture of such compounds, and dissolved therein ii) at least one compoumd of the formula I $$[M^{+n}(L)_x]^{n+}nX^- \qquad (I)$$

in which n is 2 or 3, M is a metal cation selected from the group consisting of $Zn^{2+}$, $Mg^{2+}$, $Fe^{2+}$, $Co^{2+}$, $Ni^{2+}$, $Cr^{2+}$, $Ru^{2+}$, $Mn^{2+}$, $Sn^{2+}$, $VO^{2+}$, $Fe^{3+}$, $Al^{3+}$ and $Co^{3+}$, $X^-$ is an anion which is selected from the group consisting of $AsF_6^-$, $SbF_6^-$, $BiF_6^-$ and derivatives derived from these anions in which a fluorine atom is replaced by hydroxyl groups, or in which up to 50% of the anions $X^-$, based on the total amount of anions, can also be any desired anions, L is water or an organic σ-donor ligand which contains, as ligand sites, one or more functional radicals selected from the group consisting of —CO—, —CO—O—, —O—CO—O— and —O—, and which forms σ-bonds with the central atom via the oxygen atom or via the oxygen atoms, and x is an integer from 0 to 6, it being possible for the ligands L to differ within the context of the definitions given.

12 Claims, No Drawings

INITIATORS FOR MATERIALS WHICH CAN BE POLYMERIZED CATIONICALLY

The present invention relates to novel initiator compositions for material which can be polymerized cationically, selected novel metal complexes, processes for the preparation of the initiator compositions and the metal complexes, materials which can be polymerized cationically and contain these initiator compositions, a process for the preparation of hardened products using the novel initiator compositions and the hardened products.

Hardenable compositions which contain materials which can be polymerized cationically, preferably epoxy resins, and metallocene salts as hardening agents are described in EP-A-94,915 and -109,851.

In these compositions which are already known, the organometallic complex salts are in general activated by irradiation with actinic radiation after being mixed into the material to be polymerized and before hardening by heat, it being possible for partial polymerization to take place, depending on the material and radiation conditions, and the compositions are then hardened by means of heat, or the compositions are hardened directly at high temperatures, as a rule at close to the decomposition point of the complex salt.

For a number of uses, for example for use in covering processes in the production of integrated circuits or as rapidly hardening one-component adhesives, hardenable compositions are required which combine properties which are in themselves opposite and are therefore difficult to realize with one another, such as adequate processing stability of the non-hardened composition (pot life) and the fastest possible rate of hardening at the lowest possible temperatures.

Epoxy-based encapsulating systems which can be hardened rapidly are known from EP-A-235,077. These systems contain selected diglycidyl ethers, hardening catalysts, sterically hindered phenols or phosphites and certain reactive diluents. A zinc tetrafluoroborate complex which contains water and tetrahydrofuran as ligands is described as the hardening catalyst. The concentration of the hardener must in general be adjusted precisely in order to achieve adequate processing stability combined with a high rate of hardening.

Initiators for compounds which can be polymerized cationically have now been found, which are employed in combination with a reactive diluent so that control of the initiator activity is possible. Such initiator systems can be processed in a simple manner and moreover lead to crosslinked products having advantageous final properties.

The high heat stability of the hardened product is to be regarded in particular as surprising. In addition, the products hardened with these initiator compositions are distinguished by a good colour stability and by an unexpectedly firm bonding of the initiator constituents to the hardened resin, and thus by a low degree of corrosion. Ions of the initiator are thus not washed out of the resin in the "pressure cooker test" (20 g of powdered sample are boiled together with 100 ml of deionized water at 121° C./1.2 bar for 20 hours; the electrical conductivity of the water is then determined). Another advantage of the initiator compositions according to the invention is the high throughputs which can be achieved, especially during mechanical processing, since rapid gelling is possible at low temperatures and also since the after-hardening times at a higher temperature can be cut short. The initiator action is furthermore retained after the hardening process is interrupted, so that the hardening reaction starts up again on renewed heating up. The fact that the mixing ratio of the resin and hardener components is in general not critical for the hardening conditions is to be regarded as a further advantage during processing of the hardenable compositions according to the invention. This mixing ratio can thus be varied, especially during mechanical processing, without the hardening conditions having to be adjusted each time.

Activation of the hardenable compositions by irradiation before the hardening step can furthermore be dispensed with for the novel initiator compositions, so that a simplification during processing generally results, especially in systems having a high filler content or in the case of hardening in thick layers, for which complete irradiation of the total hardenable composition may present problems.

The present invention relates to compositions of matter containing
i) an anhydride of a polycarboxylic acid, a polyisocyanate, a cyclic carbonate, a lactone or a mixture of such compounds, and dissolved therein
ii) at least one compound of the formula I $$[M^{+n}(L)_x]^{n+} nX^{-} \qquad (I)$$

in which n is 2 or 3, M is a metal cation selected from the group consisting of $Zn^{2+}$, $Mg^{2+}$, $Fe^{2+}$, $Co^{2+}$, $Ni^{2+}$, $Cr^{2+}$, $Ru^{2+}$, $Mn^{2+}$, $Sn^{2+}$, $VO^{2+}$, $Fe^{3+}$, $Al^{3+}$ and $Co^{3+}$, $X^-$ is an anion which is selected from the group consisting of $AsF_6^-$, $SbF_6^-$, $BiF_6^-$ and derivatives derived from these anions in which some of the atoms fluorine are replaced by hydroxyl groups, or in which up to 50% of the anions $X^-$, based on the total amount of anions, can also be any desired anions, L is water or an organic σ-donor ligand which contains, as ligand sites, one or more functional radicals selected from the group consisting of —CO—, —CO—O—, —O—CO—O— and —O—, and which forms σ-bonds with the central atom via the oxygen atom or via the oxygen atoms, and x is an integer from 0 to 6, it being possible for the ligands L to differ within the context of the definitions given.

The expression "up to 50% of the anion $X^-$ can also be any desired anions" is to be understood as meaning that in compounds of the formula I about half the total anions present can have any desired meaning. The possible content of anions which differ from $AsF_6^-$, $SbF_6^-$, $BiF_6^-$ or derivatives thereof containing hydroxyl groups depends on the desired activity of the initiator compositions. A compound of the formula I containing anions which differ from $AsF_6^-$, $SbF_6^-$, $BiF_6^-$ or derivatives thereof containing hydroxyl groups is regarded as usable for the purposes of the present invention if, in combination with component i), it is capable of hardening a material which can be polymerized cationically. This can be determined by the expert by routine studies.

The term "organic σ-donor ligand" is to be understood as meaning that L is any σ-donor ligand which forms a metal-ligand σ-bond via an oxygen atom of the functional groups defined above. The term "σ-donor ligand" is to be understood here in the broadest sense, as defined, for example, in R. P. Houghton, Metal Complexes In Organic Chemistry, page 4, Cambridge University Press, 1979. The systems here can thus be pure σ-donors, σ- and π-donors or σ-donors and π-acceptors.

The size of the index x describes the number of ligands L. This number in general depends on the extent to which the central atom $M^{+n}$ is saturated by coordination and on how many ligand sites a particular ligand has. For the purposes of the present invention, compounds of the formula I in which the central atom is not saturated, partly saturated or completely saturated by coordination can be employed. The number of ligands L can be between zero and six. In the case where the compound of the formula I contains ligands L and the central atom is saturated by coordination, x assumes a value, depending on the number of ligand sites in L, such that the central atom is complexed with eight or in particular with six oxygen atoms of the ligand sites of the ligand or ligands L. In the case of selected ligands, more than eight oxygen atoms can also complex the central atom. Thus if L is a monodentate ligand, x is in general six, in the case of bidentate ligands x is in general three, in the case of tridentate ligands x is in general two and in the case of tetradentate or more highly dentate ligands x is in general one or two.

Examples of possible ligand types L are alcohols, including phenols, water, ethers, aldehydes, ketones, ketenes, acetals, acylals, acyloins, carboxylic acids or functional derivatives of carboxylic acids, for example esters or anhydrides thereof, including lactones and cyclic carbonates, and hydroxycarboxylic acids and oxocarboxylic acids and esters and anhydrides thereof.

Of these ligands, water, ethers, ketones, carboxylic acid anhydrides and carboxylic acid esters, in particular the lactones and anhydrides of dicarboxylic acids, are particularly preferred.

The carboxylic acid, anhydride or ester ligands L are quite generally aliphatic, cycloaliphatic, aromatic or araliphatic compounds having one or more than one carboxyl group in the molecule.

The preferred number of carbon atoms is 2 to 40 in the aliphatic carboxylic acids and 7 to 12 in the cycloaliphatic, aromatic and araliphatic carboxylic acids.

Examples of compounds having a carboxyl group in the molecule are saturated and unsaturated aliphatic monocarboxylic acids, such as acetic acid, propionic acid, butyric acid, valeric acid, isovaleric acid, pivalic acid, caproic acid, lauric acid, myristic acid, palmitic acid, stearic acid, arachic acid or acrylic acid, methacrylic acid, propiolic acid, crotonic acid, isocrotonic acid, tetraolic acid, sorbic acid or oleic acid; or cycloaliphatic monocarboxylic acids, such as cyclohexanecarboxylic acid; or aromatic monocarboxylic acids, such as benzoic acid, naphthoic acids or tolylic acids; or araliphatic monocarboxylic acids, such as hydrotropic acid, atropic acid or cinnamic acid.

Examples of compounds containing more than one carboxyl group in the molecule are saturated aliphatic dicarboxylic acids, such as oxalic acid, malonic acid, succinic acid, α-methylsuccinic acid, glutaric acid, adipic acid, pimelic acid, suberic acid, azelaic acid, sebacic acid or dimerized linoleic acid; or unsaturated aliphatic dicarboxylic acids, such as maleic acid, fumaric acid, mesaconic acid, citraconic acid, glutaconic acid or itaconic acid; or cycloaliphatic dicarboxylic acids, such as camphoric acid, hexahydrophthalic, hexahydroisophthalic or hexahydroterephthalic acid, tetrahydrophthalic, tetrahydroisophthalic or tetrahydroterephthalic acid or 4-methyltetrahydrophthalic acid, 4-methylhexahydrophthalic acid or endomethylenetetrahydrophthalic acid; or aromatic dicarboxylic acids, such as phthalic, isophthalic or terephthalic acid; or tricarboxylic and higher carboxylic acids, such as aromatic tri- or tetracarboxylic acids, for example trimellitic acid, trimesic acid, pyromellitic or benzophenonetetracarboxylic acid.

The anhydrides as a rule have one or two anhydride groups in the molecule. They can be intramolecular anhydrides or intermolecular anhydrides. The intermolecular anhydrides can be anhydrides of the same or different carboxylic acids. Examples of such ligands are the anhydrides of the carboxylic acids listed above.

If L is an ester, this is in general derived from an aliphatic, cycloaliphatic, aromatic or araliphatic mono- or polycarboxylic acid, which as a rule is esterified with a monohydric aliphatic, cycloaliphatic, aromatic or araliphatic alcohol.

Suitable mono- or polycarboxylic acids for the preparation of these esters are listed above.

Examples of alcohols which can be employed as ligands L or for the esterification are monohydric aliphatic alcohols having 1 to 20 carbon atoms, such as methanol, ethanol, n-propanol, isopropanol, butanol, pentanol, hexanol, octanol, decanol, dodecanol, tetradecanol, hexadecanol, octadecanol or eicosanol, monohydric cycloaliphatic alcohols having 5 to 12 carbon atoms, such as cyclopentanol or cyclohexanol, or monohydric phenols having 6 to 14 carbon atoms, such as phenol, cresols or naphthols.

The esters also include, in particular, lactones, especially lactones of aliphatic hydroxycarboxylic acids, such as γ-butyrolactone, γ-valerolactone, δ-valerolactone, ε-caprolactone or crotonolactone, or cyclic carbonates. If L is a cyclic carbonate, this is in general understood as meaning an aliphatic compound having a carbonate group. The preferred number of carbon atoms is 5 to 12. An example of such ligands L is γ-propylene carbonate.

If L is an ether, this is in general derived from a mono- to tetrahydric aliphatic, cycloaliphatic, aromatic or araliphatic alcohol. Such ethers can contain free hydroxyl groups. The ether group can be part of a carbon chain or is part of a ring system.

Ligands L having ether groups as part of a carbon chain are derived, for example, from monohydric alcohols. Such alcohols are listed above, for example, as esterification components of the ester ligands L.

Examples of ligands L having ether groups as part of a carbon chain based on polyhydric alcohols are the polyalkyl ethers, in particular the di-, tri- or tetramethyl, -ethyl, -propyl or -butyl ethers, of aliphatic di-, tri- or tetraols, such as ethylene glycol, diethylene glycol and higher poly-(oxyethylene)glycols, propane-1,2-diol, propane-1,3-diol or higher poly-(oxypropylene)-glycols, butane-1,4-diol or higher poly-(oxybutylene)-glycols, pentane-1,5-diol, neopentylglycol(2,2-dimethylpropanediol), hexane-1,6-diol, octane-1,8-diol, decane-1,10-diol, dodecane-1,12-diol, hexane-2,4,6-triol, glycerol, 1,1,1-trimethylolethane, 1,1,1-trimethylolpropane or pentaerythritol; or the dimethyl, -ethyl, -propyl or -butyl ethers of cycloaliphatic diols, such as 1,3- or 1,4-dihydroxycyclohexane, 1,4-cyclohexanedimethanol, bis-(4-hydroxycyclohexyl)-methane, 2,2-bis-(4-hydroxycyclohexyl)-propane or 1,1-bis-(hydroxymethyl)-cyclohex-3-ene; or the di-, tri- or tetramethyl, -ethyl, -propyl or -butyl ethers of di-, tri- or tetraphenols or mono- or polynuclear polyphenols, such as resorcinol, hydroquinone, bis-(4-hydroxyphenyl)-methane, 2,2-bis-(4-hydroxyphenyl)-propane, bis-(4-hydroxyphenyl)ether, bis-(4-hydroxyphenyl) sulfone, 1,3,5-trihydroxybenzene or 1,1,2,2-tetrakis-(4-hydroxyphenyl)-ethane. These polyhydric alcohols or phenols can also themselves be employed as ligands L.

Ligands L having ether groups as part of a ring system are derived from polyhydric alcohols, in particular from diols. Examples of such ligands are tetrahydrofuran, dioxane or crown ethers, such as 18-crown-6, 15-5 or 12-crown-4.

Preferred ether ligands contain two or in particular one ether group in the molecule. Cyclic ether ligands are particularly preferred.

If L is an aldehyde, the compound is an aliphatic, cycloaliphatic, aromatic or araliphatic compound having preferably one or two aldehyde groups in the molecule. Examples of these are aldehydes of the carboxylic acids listed above.

If L is a ketone, the compound is an aliphatic, cycloaliphatic, aromatic or araliphatic compound having preferably one or two keto groups in the molecule. The ketone group can be part of a carbon chain or is part of a ring system. The term "ketone" also includes quinones.

Examples of aliphatic ketones are acetone, methyl ethyl ketone, ethyl propyl ketone, diisopropyl ketone and hexane-2,4-dione.

Examples of cycloaliphatic ketones are 1,4-benzoquinone, cyclopentanone or cyclohexanone.

Examples of aromatic ketones are 1,4-naphthoquinone, anthraquinone or benzophenone.

Examples of araliphatic ketones are acetophenone, propiophenone, chalcone or desoxybenzoin.

Ligands L which have several different ligand sites in one molecule are also possible. An example of this is 2-methoxyethanol.

If some of the anions $X^-$ in a compound of the formula I have any desired meaning, these can be, for example, sulfate, phosphate, halide, carboxylate or sulfonate anions. They are preferably chloride or fluoride.

Preferred components ii) include compounds of the formula II

$$[(L^1)_a M^{+n} (L^2)_b]^{n+} nX^- \quad (II)$$

in which M, X and n are as defined above, $L^1$ is a mono- to hexadentate σ-donor ligand and is an aliphatic, cycloaliphatic, aromatic or araliphatic compound having one or two ketone, anhydride, carbonate or ester groups or one to six ether groups per molecule, it being possible for the ligands $L^1$ of a compound of the formula II to differ in the context of the definitions given, $L^2$ is water, b is an integer from 0 to 2, preferably 0, and, if $L^1$ is a monodentate ligand, a is an integer from 4 to 6 and the sum of a and b is in each case 6, and if $L^1$ is a bidentate ligand, a is an integer from 2 to 3 and the sum of 2a and b is in each case 6, and if $L^1$ is a tridentate ligand, a is 1 or 2 and the sum of 3a and b is 6, and if $L^1$ is a tetra-, penta- or hexadentate ligand, a is 1 and the sum of 4a and b or of 5a and b or of 6a and b is 6 or 8.

Component i) of the initiator compositions according to the invention is an anhydride of a polycarboxylic acid, a polyisocyanate, a cyclic carbonate or a lactone. Examples of anhydrides of a polycarboxylic acid, cyclic carbonates or lactones are listed above as possible ligands L.

If component i) is a polyisocyanate, in general any aliphatic, cycloaliphatic, aromatic or araliphatic compound having at least two isocyanate groups or isocyanate groups which are blocked and can be deblocked by heating, and in which component ii) can be dissolved, can be used.

Preferred polyisocyanates contain three or in particular two isocyanate groups and have 6 to 20 carbon atoms. Aromatic diisocyanates, in particular 4,4'-diisocyanatodiphenylmethane and industrial mixtures of different diisocyanatodiphenylmethanes, are especially preferred.

Polyisocyanates are particularly preferred as components i) since hardened products having particularly high glass transition temperatures can as a rule be prepared with such initiator compositions.

Examples of preferred polyisocyanates are 2,4-diisocyanatotoluene and industrial mixtures thereof with 2,6-diisocyanatotoluene, 2,6-diisocyanatotoluene, 1,5-diisocyanatonaphthalene, 4,4'-diisocyanatodiphenylmethane and industrial mixtures of various diisocyanatodiphenylmethanes (for example the 4,4'-and 2,4'-isomers), urethanized 4,4'-diisocyanatodiphenylmethane, carbodiimidized 4,4'-diisocyanatodiphenylmethane, the uretdione of 2,4-diisocyanatotoluene, triisocyanatotriphenylmethane, the adduct of diisocyanatotoluene and trimethylolpropane, the trimer of triisocyanatotoluene, diisocyanato-m-xylylene and N,N'-di-(4-methyl-3-isocyanatophenyl)-urea, mixed trimerization products of diisocyanatotoluene and 1,6-diisocyanatohexamethylene, 1,6-diisocyanatohexane, 3,5,5-trimethyl-1-isocyanatomethylcyclohexane (isophorone diisocyanate), N,N',N''-tri-(6-isocyanatohexyl)-biuret, 2,2,4-trimethyl-1,6-diisocyanatohexane, 1-methyl-2,4-diisocyanatocyclohexane, dimeryl diisocyanate, 4,4'-diisocyanatodicyclohexylmethane, trimeric isophorone diisocyanate, trimeric hexane diisocyanate and methyl 2,6-diisocyanatohexanoate.

Preferred components i) are anhydrides of polycarboxylic acids, in particular those anhydrides which are known per se as epoxy hardeners. Anhydrides of dicarboxylic acids are particularly preferably used. Examples of such preferred components i) are tetrahydrophthalic anhydride, methyl-tetrahydrophthalic anhydride, hexahydrophthalic anhydride and in particular methyl-hexahydrophthalic anhydride.

The amount of compound of the formula I is in general chosen so that, in combination with a hardenable material, a processing stability and rate of hardening which are adequate for the particular intended use result. The amount required in an individual case can be determined by simple experiments. The amount of component ii) in general varies between 0.05 and 10% by weight, based on the total weight of components i) and ii).

With the exception of bis-{[12]-crown-4}-iron(II)hexafluoroantimonate, bis-{[15]-crown-5}-iron(II)hexafluoroantimonate, and ([12]-crown-4)([15]-crown-5)-iron(II)hexafluoroantimonate, the compounds of the formula II are novel and the present invention likewise relates to these.

The compounds which are already known are described in Angew. Chem., 97 (10), pages 879–80 (1985). No intended use of these compounds is stated.

The index n is preferably 2.

Initiator compositions of compounds of the formula II in which b is 0 or these compounds are preferred.

Initiator compositions of compounds of the formula II in which a is 6 or 3 or these compounds are preferred.

M is preferably a metal cation selected from the group consisting of $Fe^{2+}$, $Zn^{2+}$, $Mg^{2+}$, $Co^{2+}$, $Mn^{2+}$, $Sn^{2+}$ and $Al^{3+}$.

M especially preferably is a metal cation selected from the group consisting of $Zn^{2+}$, $Mn^{2+}$, $Sn^{2+}$, $Al^{3+}$ and in particular $Fe^{2+}$.

Compounds of the formula I or II in which all the anions $X^-$ are selected from the group consisting of $AsF_6^-$, $SbF_6^-$, $SbF_5(OH)^-$ and $BiF_6^-$ are preferably used for the preparation of the initiator compositions according to the invention. The preferred anion $X^-$ is $SbF_6^-$.

Preferred initiator compositions are liquid at temperatures below 50° C., in particular below 30° C., in order to facilitate incorporation into the material which can be polymerized cationically.

Particularly preferred initiator compositions contain as component i) anhydrides of polycarboxylic acids, in particular dianhydrides of polycarboxylic acids.

Although the composition of the initiator compositions according to the invention is not known specifically, it is assumed that on dissolving in component i) the ligand L in component ii) is replaced by this component present in excess, in particular by anhydride ligands.

The anhydride complexes of the formula I are particularly preferred, and the compounds of the formula II in which a is 6 or 3, b is 0 and $L^1$ is an aliphatic, cycloaliphatic, aromatic or araliphatic compound having one or two carboxylic acid anhydride groups are especially preferred.

Compounds which are liquid at temperatures below 50° C., in particular below 30° C., are particularly preferred as component i). The component can also be liquid mixtures of such compounds.

The compositions according to the invention can be prepared by dissolving compounds of the formula I in a component i) as defined above.

The compounds of the formula I or II can in general be obtained by various processes a) to e).

The compounds of the formula II in which M is $Fe^{2+}$ and b is 0 can be obtained, for example, by process a). For this, a π-complex of the formula III $$[(R^1)Fe^{+2}(R^2)]^{+a}{}_aX^- \quad (III)$$

in which $R^1$ is a π-arene and $R^2$ is an anion of a π-arene, for example a cyclopentadienyl anion, or in particular is a π-arene, a is 1 or 2 and $X^-$ is as defined above, is dissolved in a ligand $L^1$ as defined above, which is to be introduced, or in a mixture of these compounds and the solution is irradiated with actinic radiation or heated until the ligand exchange of $R^1$ and $R^2$ for $L^1$ has essentially taken place, and the product is then separated off from the reaction mixture in a manner which is known per se.

The conversion of the compound of the formula III can be monitored by chromatographic or spectroscopic methods in a manner which is known per se, for example by monitoring the intensity of an absorption band characteristic of the starting complex of the formula III.

The amount of starting substance of the formula III and ligand $L^1$ to be introduced are in general chosen so that preferably ten to one hundred mol of the compound L are present per mol of compound of the formula III.

The reaction can be carried out by heating, depending on the stability of the starting complex. However, the reaction can also be carried out by irradiation of the starting complex of the formula III with actinic radiation, a wavelength at which the starting complex absorbs being used.

The product of the formula II in general crystallizes out in the reaction mixture during the irradiation or during cooling, or can be precipitated from the reaction mixture by addition of a non-solvent for the product. The product is then removed from the mixture by means of routine operations, such as filtration or extraction.

The starting compounds of the formula III are known per se and are described, for example, in EP-A-94,915.

For carrying out process b) a metal halide of the formula IV together with an approximately stoichiometric amount of a silver salt of the formula V $$M^{+n}(Hal)_n \quad (IV),$$

$$AgX \quad (V)$$

in which n, M and X are as defined above and Hal is a halide anion, in particular chloride or fluoride, are dissolved or suspended in a ligand $L^1$ as defined above, which is to be introduced, or in a mixture of these compounds and if appropriate the reaction mixture is heated, so that the product of the formula II is formed.

The amounts of starting substances of the formula IV and V and of ligand $L^1$ to be introduced are in general chosen so that about n mol of the compound of the formula V and about ten to about one hundred mol of the compound $L^1$ are present per mol of compound of the formula IV.

The reaction is in general carried out at a low temperature, for example at 20°–40° C. The product can in this case likewise be separated off from the reaction mixture by means of routine operations, for example by filtering off the silver halide formed and isolating the product formed, as described under process a).

To carry out process c) a metal salt of the formula VI is reacted with a compound of the formula VII $$M^{+n}(Y^-)_{n'} \quad (VI)$$

$$\left[ \begin{array}{c} R_3 \\ \phantom{R}\diagdown \\ \phantom{RR}O\text{—}R_4 \\ \phantom{R}\diagup \\ R_5 \end{array} \right]^+ X^- \quad (VII)$$

in which $R_3$, $R_4$ and $R_5$ independently of one another are alkyl, cycloalkyl or aralkyl, in particular methyl or ethyl, M, n and $X^-$ are as defined above and $Y^-$ is a halide anion, alcoholate anion or carboxylic acid anion, together with a compound $L^1$ as defined above, so that the product of the formula II is formed.

The amount of starting substances of the formulae VI and VII and of ligand $L^1$ to be introduced are in general chosen so that n mol of the compound of the formula VII and preferably ten to one hundred mol of the compound $L^1$ are present per mol of compound of the formula VI.

The reaction is carried out at room temperature or by heating, for example in a temperature range from 20°–100° C. The product can in this case likewise be separated off from the reaction mixture by means of routine operations, for example as described for reaction a).

The compounds of the formula VII are known per se and are described, for example, in U.S. Pat. No. 3,585,227 or in J. Chem. Soc., Chem. Communications, 1976, pages 33-4.

For carrying out process d), a compound of the formula VIII is reacted with a Lewis acid of the formula IX $$M^{+n}F_n \quad \text{(VIII)},$$

$$QF_5 \quad \text{(IX)}$$

in which n and M are as defined above and Q is As, Sb or Bi. For this, the compound of the formula VIII can be dissolved in an excess of the compound of the formula IX, or the reaction is carried out in a solvent which is inert under the reaction conditions and is capable of dissolving at least one of the compounds of the formula VIII or IX. Examples of suitable solvents are liquid $SO_2$ or anhydrous HF. The reaction product in general crystallizes out of the reaction solution and can be separated off from the mixture by routine processes, such as filtration.

The resulting product can be employed as such for the preparation of the initiator compositions according to the invention by dissolving it in a component i) as defined above, or the product is dissolved in a ligand L as defined above, which is to be introduced, or in a mixture of these ligand and if appropriate the reaction mixture is heated so that the ligand L is introduced into the compound of the formula I. The product can then be isolated and purified in the same manner as described for process a).

Reaction of compounds VIII and IX are described by D. Gantar et al. in J. Chem. Soc., Dalton Transactions, 1987, pages 2379-83.

The amount of starting substances of the formulae VIII and IX and of ligand L to be introduced are in general chosen so that n mol of the compound of the formula IX and preferably ten to one hundred mol of the compound L are present per mol of compound of the formula VII. The reaction is carried out at room temperature or by heating, for example in a temperature range from 20°-200° C.

The variant of process d) for the preparation of the initiator compositions according to the invention in which the reaction product of the compounds VIII and IX are dissolved directly, after isolation thereof, in component i) is particularly preferred.

According to process e), the compounds of the formula II can also be converted into other compounds of the formula II by ligand exchange. For this, a compound of the formula IIa $$[(L^3)_a M^{+n}(L^2)_b]^{n+} nX^- \quad \text{(IIa)}$$

in which M, $L^2$, X, n, a and b are as defined above and $L^3$ is as defined above for $L^1$, is dissolved together with an amount corresponding to at least the stoichiometry of the desired end product of a ligand $L^1$ which differs from $L^3$, the solution is heated to carry out the ligand exchange and the product of the formula II in which all or some of the original ligand $L^3$ is replaced by the newly introduced ligand $L^1$ is isolated and worked up in the manner described under process a).

The amounts of starting substance of the formula IIa and ligand $L^1$ to be introduced are selected according to the stoichiometry of the desired product. For example, if only some of the ligand $L^3$ in the starting substance is to be exchanged, less than the stoichiometric amount of ligand $L^1$ to be introduced is used. This amount also in general depends on the size of the complex formation constant of the product and can be determined by the expert by routine processes.

If all the ligands $L^3$ in the starting substance of the formula IIa are to be exchanged, the ligand $L^1$ to be introduced is as a rule initially used in the stoichiometric amount or in a stoichiometric excess. Here also, the amount of $L^1$ in general also depends on the size of the complex formation constant of the product and is determined by the expert with the aid of routine processes. About ten to one hundred mol of the ligand $L^1$ are preferably employed per mol of the compound IIa.

The present invention likewise relates to the processes a) to e).

The compounds of the formulae I and II are in general hygroscopic. The water-containing compounds of the formulae I and II can be prepared by storage of the anhydrous compounds of the formula I in air or by reaction of these compounds with water.

The compounds of the formula I having a central atom M which is not or only partly saturated by coordination can as a rule be obtained from the compounds saturated by coordination by heating. In this procedure, the ligand L is distilled off and the compound having the central atom which is not or only partly complexed is thus obtained.

The compounds of the formula I are distinguished by a high reactivity, and for this reason they are in general used in dilution with a component i) as described above. The particular desired reactivity of the initiator composition can be established simply and reproducibly by varying the amount of compounds of the formula I.

The initiator compositions according to the invention can be combined with organic materials which can be polymerized cationically to give hardenable compositions having the advantageous properties described above. Thus, for example, the very highly reactive compounds of the formula I can be diluted with component i) and the monomer which can be polymerized cationically to the extent that the content thereof makes up only 1% of the mixture.

The invention therefore also relates to hardenable compositions containing a) an organic material which can be polymerized cationically and b) an initiator composition as defined above.

The processing stability of such a hardenable composition can be adjusted, for example, via the amount of initiator composition or the content of active component ii) so that a storage stability which is adequate for processing is obtained at low temperatures.

The amount of initiator component b) is as a rule 0.05 to 0.5 part by weight, preferably 0.15-0.3 part by weight per part by weight of material which can be polymerized cationically.

Components a) and b) are as rule mixed at low temperatures, for example below 50° C., in order to avoid premature gelling or hardening.

Organic materials which can be polymerized cationically and can preferably be employed are ethylenically unsaturated compounds which can be polymerized cationically, such as certain mono- or diolefins, or vinyl ethers, for example methyl vinyl ether, isobutyl vinyl ether, trimethylolpropane trivinyl ether, ethylene glycol divinyl ether, 3,4-dihydro-2-formyl-2H-pyran and the 3,4-dihydro-2-formyl-2H-pyran-2-carboxylic acid ester of 2-hydroxymethyl-3,4-dihydro-2H-pyran, or vinyl esters, such as vinyl acetate or vinyl stearate, or heterocyclic compounds which can be polymerized cationically, such as cationically polymerizable cyclic ethers or methylol compounds.

Further examples of organic materials which can be polymerized cationically are described in the above-mentioned EP-A-94,915.

Hardenable compositions in which component a) is a cyclic ether which can be polymerized cationically are preferred.

The especially preferred components a) include the epoxy resins.

The invention thus particularly relates to hardenable compositions containing a compound having on average at least two 1,2-epoxide groups per molecule, as component a), and component b) as defined above.

A large number of common epoxy resins can be employed as component a). The compounds can be employed by themselves or as a mixture of several epoxy resins or also in combination with other monomers which can be hardened by component b).

Examples of epoxy resins are:

I) Polyglycidyl and poly-($\beta$-methylglycidyl) esters which can be obtained, for example, by reaction of a compound containing at least two carboxyl groups in the molecule with epichlorohydrin, glycerol-dichlorohydrin or $\beta$-methylepichlorohydrin in the presence of bases.

Examples of compounds having at least two carboxyl groups in the molecule are the polycarboxylic acids, such as have already been described above as components for the preparation of the ester ligand L.

II) Polyglycidyl and poly-($\beta$-methylglycidyl) ethers which can be obtained, for example, by reaction of a compound containing at least two alcoholic hydroxyl groups and/or phenolic hydroxyl groups in the molecule with epichlorohydrin, glycerol-dichlorohydrin or $\beta$-methylepichlorohydrin under alkaline conditions or in the presence of an acid catalyst with subsequent treatment with an alkali. Examples of compounds having at least two alcoholic hydroxyl groups and/or phenolic hydroxyl groups in the molecule are the polyhydric alcohols which have already been described above as components for the preparation of the ether ligand L; or alcohols containing aromatic groups, such as N,N-bis-(2-hydroxyethyl)-aniline; or novolaks, which are obtainable by condensation of aldehydes, such as formaldehyde, acetaldehyde, chloral or furfuraldehyde, with unsubstituted or alkyl- or halogen-substituted phenols, such as phenol, the bisphenols described above, 2- or 4-methylphenol, 4-tert-butylphenol, p-nonylphenol or 4-chlorophenol.

III) Poly-(S-glycidyl) compounds, such as, for example, di-S-glycidyl derivatives which are derived from dithiols, such as ethane-1,2-dithiol, or from bis-(4-mercaptomethylphenyl) ether.

IV) Epoxidation products of dienes or polyenes, such as cycloaliphatic epoxy resins which can be prepared, for example, by epoxidation of ethylenically unsaturated cycloaliphatic compounds. Examples of these are 1,2-bis-(2,3-epoxycyclopentyloxy)-ethane, 2,3-epoxycyclopentyl glycidyl ether, bis-(2,3-epoxycyclopentyl) ether, 5(6)-glycidyl-2-(1,2-epoxyethyl)-bicyclo[2.2.1]heptane, dicyclopentadiene dioxide, 3,4-epoxy-6-methylcyclohexylmethyl 3',4'-epoxy-6'-methylcyclohexanecarboxylate or 3,4-epoxycyclohexylmethyl 3',4'-epoxycyclohexanecarboxylate.

However, epoxy resins in which the 1,2-epoxide groups are bonded to different hetero atoms or functional groups can also be used; such compounds include, for example, the glycidyl ether glycidyl esters of salicylic acid.

The hardenable compositions according to the invention can be obtained in any desired form, for example as homogeneous liquid or solid mixtures. These compositions can be hardened directly by heat, the hardening temperatures in general being substantially below those of the compositions already known.

The preferably liquid initiator components can be mixed into the cationically polymerizable organic material by customary means, such as with stirrers, mills or kneaders, preferably at temperatures below 50° C.

Hardening is preferably carried out below 220° C., in particular in the range from 180° to 200° C. However, preliminary hardening can also be carried out at lower temperatures until the hardenable composition gels, this then being followed by complete hardening at higher temperatures.

The hardened products are distinguished by good mechanical and electrical end properties, in particular by the advantageous end properties described above.

The invention thus also relates to a process for the preparation of hardened products, which comprises hardening a hardenable composition according to the invention by heating; the invention furthermore relates to the hardened products obtainable by heating the hardenable compositions according to the invention.

If desired, reactive diluents, for example styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary aliphatic monocarboxylic acids, can be added to the hardenable compositions to reduce the viscosity.

The compositions according to the invention can furthermore contain, as other customary additives, plasticizers, extenders, fillers and reinforcing agents, for example coal tar, bitumen, textile fibres, glass fibres, asbestos fibres, boron fibres, carbon fibres, mineral silicates, mica, quartz flour, hydrated aluminium oxide, Bentonite ®, wollastonite, kaolin, silicic acid aerogel or metal powder, for example aluminium powder or iron powder, and furthermore pigments and dyes, such as carbon black, oxide colours and titanium dioxide, as well as flameproofing agents, foam suppressants, thixotropic agents, flow control agents (some of which are also used as mould release agents), such as silicones, waxes and stearates, or tackifying agents, antioxidants and light stabilizers.

The amount of additives is usually 0–70 parts by weight per 100 parts by weight of the hardenable composition.

The hardenable compositions according to the invention can be employed quite generally for the preparation of hardened products, and can be employed in the formulation suitable to the particular specific field of use, for example as coating compositions, varnishes, pressing compositions, dipping resins, casting resins, impregnating resins, laminating resins, adhesives or matrix resins.

The hardenable compositions according to the invention can be employed in particular as a covering material for active and passive electronic components or for the production of insulating materials or shaped articles.

The invention also relates to the use of the hardenable mixtures for the abovementioned purposes.

The present examples illustrate the invention.

The $^1$H-NMR spectra are measured with a 100 MHz apparatus. The DSC (differential scanning calorimetry) experiments were performed using a Mettler TA 3000 DSC apparatus. The heating up rate here is 10° C./minute.

I. PREPARATION OF THE COMPOUNDS OF THE FORMULA I

I.1. Preparation of hexa-(caprolactone)-iron(II) hexafluoroantimonate [process a)]

80 g (104.2 mmol) of bis-($\eta^6$-mesitylene)-iron(II) hexafluoroantimonate are dissolved in 150 ml of caprolactone and the solution is degassed under argon and exposed to a UV lamp (5000 W dust lamp), while cooling. After an exposure time of 35 minutes, the product is isolated by addition of 800 ml of dry toluene, filtered off under an inert gas, washed and dried at room temperature under a high vacuum. 118.6 g (97.8 mmol=94% of theory) of a white crystalline, very hygroscopic product are obtained.

| Elemental analysis for $C_{36}H_{60}O_{12}FeSb_2F_{12}$: | | | | | |
| --- | --- | --- | --- | --- | --- |
| | C | H | Fe | Sb | F |
| Calculated: | 35.67 | 4.99 | 4.61 | 20.09 | 18.81; |
| Found: | 35.59 | 4.95 | 5.00 | 21.30 | 18.55; |

IR (KBr): strong band at 660 cm$^{-1}$ (SbF$_6^-$); the other main bands in the IR spectrum largely correspond to those of caprolactone;

$^1$H-NMR (D$_2$O): signals at: 4.36 ppm (2H); 2.67 ppm (2H); and 1.77 ppm; DSC: endothermic decomposition at 240° C.

I.2. Preparation of tris-(ethylene glycol dimethyl ether)-iron(II) hexafluoroantimonate [process a)+e)]

2 g (2.6 mmol) of bis-($\eta^6$-mesitylene)-iron(II) hexafluoroantimonate are dissolved in 8 ml of dry acetone and the solution is degassed under argon. The red solution is cooled and exposed to a UV lamp (5000 W dust lamp). After about 5 minutes, the solution is completely decolorized. 5 ml of ethylene glycol dimethyl ether are added. The acetone is removed under a vacuum and the crystals formed are filtered off under an inert gas and washed three times with toluene. After drying under a high vacuum at room temperature, 2.01 g (2.52 mmol=97% of theory) of white, very hygroscopic crystals result.

| Elemental analysis for $C_{12}H_{30}O_6FeSb_2F_{12}$: | | |
| --- | --- | --- |
| | C | H |
| Calculated: | 18.07 | 3.79; |
| Found: | 16.80 | 3.96; |

$^1$H-NMR (D$_2$O): 3.62 ppm singlet (2H); 3.37 ppm singlet (3H).

I.3. Preparation of bis-(diethylene glycol dimethyl ether)-iron(II) hexafluoroantimonate [process a)+e)]

2.0 g (2.51 mmol=96% of theory) of the abovementioned compound are obtained in a manner analogous to that in Example I.2. by exposure of 2.0 g (=2.6 mmol) of bis-($\eta^6$-mesitylene)-iron(II) hexafluoroantimonate in dry acetone and subsequent addition of diglyme.

| Elemental analysis for $C_{12}H_{28}O_6FeSb_2F_{12}$: | | |
| --- | --- | --- |
| | C | H |
| Calculated: | 18.11 | 3.55; |
| Found: | 18.05 | 3.87; |

$^1$H-NMR (D$_2$O): 3.38 ppm singlet (3H); 3.66 ppm singlet (4H)

I.4. Preparation of tris-(acetic anhydride)-iron(II) hexafluoroantimonate [process a)]

15 g (19.53 mmol) of bis-($\eta^6$-mesitylene)-iron(II) hexafluoroantimonate are dissolved in 30 ml of acetic anhydride and the solution is degassed under argon. After exposure analogously to Example I.2., the solution is completely decolorized after about 20 minutes. After isolation with toluene, 15.9 g (19.07 mmol=98% of theory) of white, very hygroscopic crystals result.

| Elemental analysis for $C_{12}H_{18}O_9FeSb_2F_{12}$: | | |
| --- | --- | --- |
| | C | H |
| Calculated: | 17.28 | 2.17; |
| Found: | 16.84 | 2.45; |

IR (KBr): 1820, 1800, 1630, 1600, 1140, 1000, 900 and 660 cm$^{-1}$;

$^1$H-NMR (D$_2$O): 2.2 ppm singlet;

DSC: endothermic peaks at 130° C. (weak) and 220° C. (strong); exothermic decomposition: >270° C.

I.5. Preparation of hexa(acetone)-iron(II) hexafluoroantimonate [process a)]

40 g (52.10 mmol) of bis-($\eta^6$-mesitylene)-iron(II) hexafluoroantimonate are dissolved in 120 ml of acetone and the solution is degassed under argon. After exposure analogously to Example I.2., a completely colourless solution is formed, from which the product crystallizes out after addition of 400 ml of toluene. After filtration and washing under an inert gas, drying at room temperature under a high vacuum gives 43.5 g (49.71 mmol=95% of theory) of colourless, very hygroscopic crystals.

| Elemental analysis for $C_{18}H_{36}O_6FeSb_2F_{12}$: | | |
| --- | --- | --- |
| | C | H |
| Calculated: | 24.69 | 4.14; |
| Found: | 23.60 | 4.07; |

$^1$H-NMR (D$_2$O): 2.22 ppm singlet;

IR (KBr): 3400, 1700, 1380, 1240 and 660 cm$^{-1}$;

DSC: endothermicity 115° C.; exothermicity 173° C.

I.6. Preparation of hexa-(methylhexahydrophthalic anhydride)-iron(II) hexafluoroantimonate [process a)]

6 g (7.81 mmol) of finely powdered bis-($\eta^6$-mesitylene)-iron(II) hexafluoroantimonate are dispersed in 30 ml of methylhexahydrophthalic anhydride and partly dissolved. After degassing with argon, the solution is exposed analogously to Example I.2. until the educt has dissolved completely and the solution is completely decolorized. After addition of 100 ml of dry toluene, all the substances are soluble to give a clear solution. After addition of 200 ml of hexane (dry), the product is precipitated and the oil formed is separated off under an inert gas and washed with toluene:hexane (1:2). After drying under a high vacuum at room temperature, 9.8 g (6.37 mmol=82% of theory) of an amorphous product results.

| Elemental analysis for $C_{54}H_{72}O_{18}FeSb_2F_{12}$: | | |
|---|---|---|
| | C | H |
| Calculated: | 42.21 | 4.72; |
| Found: | 41.9 | 4.84; |

IR (KBr): strong band in the IR spectrum at 660 m$^{-1}$; the main bands in the IR spectrum correspond to those of methyl hexahydrophthalic anhydride.

I.7. Preparation of hexa-(hexahydrophthalic anhydride)-iron(II) hexafluoroantimonate [process a)]

6 g (7.81 mmol) of bis-($\eta^6$-mesitylene)-iron(II) hexafluoroantimonate are dissolved in 25 g of hexahydrophthalic anhydride at 45° C. and the solution is degassed under argon. The red solution is exposed analogously to Example I.2. until completely bleached. After addition of 50 ml of dry toluene, a clear solution is formed, from which an oil separates out by addition of 100 ml of hexane. After decanting off, washing under an inert gas and drying at room temperature under a high vacuum, 10.9 g (7.5 mmol=96% of theory) of an amorphous solid product which is hygroscopic result.

| Elemental analysis for $C_{48}H_{60}O_{18}FeSb_2F_{12}$: | | |
|---|---|---|
| | C | H |
| Calculated: | 39.69 | 4.16; |
| Found: | 39.58 | 4.60; |

$^1$H-NMR (CDCl$_3$): 3.59 ppm (2H); 2.70 ppm (4H); 2.17 and 1.90 ppm (4H);

IR (KBr): band at 660 cm$^{-1}$; the main bands in the IR spectrum correspond to those of hexahydrophthalic anhydride.

I.8. Preparation of hexa-(maleic anhydride)-iron(II) hexafluoroantimonate [process a)]

3.25 g (4.23 mmol) of bis-($\eta^6$-mesitylene)-iron(II) hexafluoroantimonate are dissolved with 6.95 g of maleic anhydride by melting the anhydride and the solution is degassed with argon and exposed for 30 minutes analogously to Example I.2. The solution does not become completely bleached. The product formed is yellowish. After addition of toluene (30 ml), a yellow crystalline product forms, which is filtered under an inert gas and washed. Drying under a high vacuum at room temperature gives 4.7 g (4.21 mmol=99% of theory) of yellow, very hygroscopic crystals, which deliquesce and decolorize in air.

| Elemental analysis for $C_{24}H_{12}O_{18}FeSb_2F_{12}$: | | |
|---|---|---|
| | C | H |
| Calculated: | 25.83 | 1.08; |
| Found: | 24.2 | 2.0; |

$^1$H-NMR (D$_2$O): singlet at 6.44 ppm;

IR (KBr): band at 660 cm$^{-1}$, the other bands largely correspond to those of maleic anhydride;

DSC: endothermic peak at 115° C. (weak) and 255° C. (strong).

I.9. Preparation of hexa-(tetrahydrofuran)-iron(II) hexafluoroantimonate [process a)]

10 g (20.97 mmol) of ($\eta^6$-cumene)($\eta^5$-cyclopentadienyl)-iron(II) hexafluoroantimonate are dissolved in 70 ml of tetrahydrofuran (dry) and the solution is degassed under argon. The yellow solution is then exposed for 30 minutes analogously to Example I.2. The product crystallizes out and is filtered off under an inert gas, washed three times with THF and dried under a high vacuum at room temperature. 9.25 g (9.636 mmol=92% of theory) of a very hygroscopic, white crystalline product which rapidly exchanges THF for water in air are obtained.

| Elemental analysis for $C_{24}H_{48}O_6FeSb_2F_{12}$ | | | | | |
|---|---|---|---|---|---|
| | C | H | Fe | Sb | F |
| Calculated: | 30.02 | 5.04 | 5.82 | 25.37 | 23.75; |
| Found: | 28.96 | 4.89 | 5.1 | 25.7 | 22.8; |

$^1$H-NMR (d$_4$-acetic acid): 2.32 ppm (singlet, 2H); 4.66 ppm (singlet, 2H);

IR (KBr): bands at 3400, 2950, 2880, 1460, 1040, 1020, 900 and 660 cm$^{-1}$;

DSC: endothermic peak at 165° C.; exothermic decomposition at 190° C.

I.10. Preparation of hexa-(dimethylmaleic anhydride)-iron(II) hexafluoroantimonate [process a)]

3 g (3.907 mmol) of bis-($\eta^6$-mesitylene)-iron(II) hexafluoroantimonate are melted with 7.6 g of freshly sublimed dimethylmaleic anhydride and the mixture is degassed under argon. It is heated to 120° C. The educt dissolves slowly and a red solution is formed, which discolours to yellow after about 10 minutes and start to crystallize out. The mixture is cooled to room temperature. Dry toluene (50 ml) is added to the solid product and the excess anhydride is dissolved. After filtration under an inert gas and washing three times, the product is dried at room temperature under a high vacuum. 4.9 g (3.81 mmol=98% of theory) of a yellow crystalline, very hygroscopic product which becomes colourless in air due to uptake of water result.

| Elemental analysis for $C_{36}H_{36}O_{18}FeSb_2F_{12}$ | | |
|---|---|---|
| | C | H |
| Calculated: | 33.67 | 2.82; |
| Found: | 30.77 | 3.34; |

$^1$H-NMR (DMSO): singlet at 1.98 ppm;

IR (KBr): very strong band at 660 cm$^{-1}$; the other bands largely correspond to those of dimethylmaleic anhydride; strong OH band at 3400 cm$^{-1}$ due to uptake of H$_2$O.

I.11. Preparation of hexa-(phthalic anhydride)-iron(II) hexafluoroantimonate [process a)]

6 g (7.81 mmol) of bis-($\eta^6$-mesitylene)-iron(II) hexafluoroantimonate are degassed in 25 g of phthalic anhydride (distilled) and the mixture is heated to 130° C. under argon. After 1 hour at 130° C., the mixture is cooled to 100° C. and 150 ml of hot toluene are added. A yellow precipitate forms and is filtered off hot under an inert gas and washed three more times with hot dry toluene. After drying under a high vacuum, 6.6 g of a yellow, hygroscopic crystalline product which becomes colourless in air result.

IR (KBr): strong band at 660 cm$^{-1}$; further bands at 3400, 1850, 1790, 1630, 1600, 1260, 1110, 910 and 540 cm$^{-1}$;

$^1$H-NMR (CDCl$_3$): signal at 7.95 ppm (multiplet, phthalic anhydride).

I.12. Preparation of hexa-(methylhexahydrophthalic anhydride)-iron(II) hexafluoroantimonate [process a)]

30.8 g (40.119 mmol) of bis-($\eta^6$-mesitylene)-iron(II) hexafluoroantimonate are finely powdered, dried at 120° C. under a high vacuum for 2 hours and then added to 102.4 g of methylhexahydrophthalic anhydride, and the solution is degassed under argon and heated to 120° C. After about 20 minutes, everything has dissolved and the red colour has disappeared. The mesitylene is then removed in vacuo (weight loss: 9.7 g). A pale brownish 49.8% solution of the above compound in the anhydride, which can be isolated analogously to Example I.6., results.

IR (KBr): strong band at 660 cm$^{-1}$; the other bands largely correspond to those of the anhydride;

| Elemental analysis for $C_{54}H_{60}O_{18}FeSb_2F_{12}$ | | |
| --- | --- | --- |
| | C | H |
| Calculated: | 42.21 | 4.72; |
| Found: | 41.53 | 4.84. |

I.13. Preparation of hexa-(caprolactone)-iron(II) hexafluoroantimonate [process a)]

26 g (33.8 mmol) of bis-($\eta^6$-mesitylene)-iron(II) hexafluoroantimonate are degassed in 50 ml of caprolactone under argon and the mixture is heated to 120° C. After 5 minutes, the red solution becomes colourless. After cooling to room temperature, the product is crystallized out by addition of 400 ml of dry toluene. After filtering and washing (toluene) under an inert gas, the product is dried at room temperature under a high vacuum. 37.8 g (31.18 mmol = 92% of theory) of white, very hygroscopic crystals result.

| Elemental analysis for $C_{36}H_{60}O_{12}FeSb_2F_{12}$: | | |
| --- | --- | --- |
| | C | H |
| Calculated: | 35.67 | 4.99; |
| Found: | 35.47 | 5.06; |

IR (KBr): The IR spectrum is identical to that of the product which has been prepared with UV light (I.1.).

The substance is identical with the compound prepared according to I.1.

I.14. Preparation of hexa-(tetrahydrofuran)-zinc(II) hexafluoroantimonate [process c)]

10 ml (22 mmol) of zinc chloride etherate in methylene chloride (2.2 mol) are added to 80 ml of dry tetrahydrofuran (THF) and the mixture is degassed under argon and cooled to 0° C. in an ice bath. 12 g (35.4 mmol) of solid triethyloxonium hexafluoroantimonate are added. The solids dissolve immediately and after about 10 minutes the product starts to crystallize out. The reaction mixture is heated to room temperature and after 4 hours the product is filtered off, washed three times with THF under an inert gas and dried under a high vacuum at room temperature. 16.3 g (16.8 mmol = 95% of theory) of colourless, very hygroscopic crystals are obtained.

| Elemental analysis for $C_{24}H_{48}O_6ZnSb_2F_{12}$: | | | | | |
| --- | --- | --- | --- | --- | --- |
| | C | H | Zn | Sb | F |
| Calculated: | 29.73 | 4.99 | 6.74 | 25.12 | 23.52; |
| Found: | 28.2 | 4.9 | 7.1 | 25.8 | 23.5; |

$^1$H-NMR (DMSO): signals at 3.95 ppm (2H, multiplet); 1.75 ppm (2H, multiplet);

IR (KBr): strong band at 660 cm$^{-1}$, further bands at 2860, 2980, 1460, 1080 and 910 cm$^{-1}$; melting point: 180°-200° C. (decomposition).

I.15. Preparation of tris-(ethylene glycol dimethyl ether)-zinc(II) hexafluoroantimonate [process c)]

1 g (2.95 mmol) of triethyloxonium hexafluoroantimonate is dissolved in 4 ml of dry ethylene glycol dimethyl ether. 0.6 ml (1.32 mmol) of zinc chloride etherate in CH$_2$Cl$_2$ (2.2. mol) is slowly added. After heating to 40° C., the product starts to crystallize out. After filtration under an inert gas and washing three times with ethylene glycol dimethyl ether, the product is dried at room temperature under a high vacuum. 0.4 g (0.5 mmol = 33% of theory) of a colourless, crystalline, very hygroscopic product results.

| Elemental analysis for $C_{12}H_{30}O_6ZnSb_2F_{12}$: | | |
| --- | --- | --- |
| | C | H |
| Calculated: | 17.85 | 3.74; |
| Found: | 16.96 | 4.17; |

$^1$H-NMR (D$_2$O): bands at 3.69 ppm (2H, singlet), 3.36 ppm (3H, singlet).

I.16. Preparation of (18-crown-6)-zinc(II) hexafluoroantimonate [process c)]

0.8 ml (1.76 mmol) of zinc chloride etherate in CH$_2$Cl$_2$ (2.2 mol) is added to 1 g of 18-crown-6, dissolved in 8 ml of CH$_2$Cl$_2$. 10 g (2.9 mmol) of triethyloxonium hexafluoroantimonate are added and the mixture is left at room temperature. After about 30 minutes, the product crystallizes out. After filtration, washing with methylene chloride and drying under a high vacuum at room temperature, 0.6 g of colourless crystals which are stable in air is obtained.

$^1$H-NMR (D$_2$O): singlet at 3.67 ppm;

IR (KBr): strong band at 660 cm$^{-1}$; further bands at 3400, 3200, 2900, 1470, 1350, 1260, 1100 (strong band), 950 and 820 cm$^{-1}$.

I.17. Preparation of tris-(ethylene glycol dimethyl ether)-iron(II) hexafluoroantimonate [process c)]

0.37 g (0.91 mmol) of FeCl$_2$ is dispersed in 10 ml of dry ethylene glycol dimethyl ether and the dispersion is degassed under argon. 2 g (5.9 mmol) of triethyloxonium hexafluoroantimonate are added. After stirring at room temperature for 2 hours, the solution becomes dark and fine crystals form. After 4 hours, the product is filtered off under an inert gas, washed three times with ethylene glycol dimethyl ether and dried at room temperature under a high vacuum. 20 g (2.51 mmol = 86% of theory) of a white, very hygroscopic crystalline compound result.

| Elemental analysis for $C_{12}H_{30}O_6FeSb_2F_{12}$: | | |
|---|---|---|
| | C | H |
| Calculated: | 18.06 | 3.79; |
| Found: | 17.70 | 4.02; |

IR (KBr): strong band at 660 cm$^{-1}$; bands at 3400, 3000, 2900, 1460, 1240 and 1050 cm$^{-1}$;

$^1$H-NMR (D$_2$O): singlet at 3.68 ppm (2H); 3.35 ppm (3H).

I.18. Preparation of bis-(ethylene glycol dimethyl ether)-manganese(II) hexafluoroantimonate [process c)]

0.33 g (2.62 mmol) of anhydrous MnCl$_2$ is suspended in 10 ml of dry ethylene glycol dimethyl ether and the suspension is degassed under argon. 2.0 g (5.9 mmol) of triethyloxonium hexafluoroantimonate are added and the mixture is stirred at room temperature. The MnCl$_2$ dissolves and fine crystals are formed. After 4 hours, the violet solution is filtered under an inert gas, washed three times with ethylene glycol dimethyl ether and dried at room temperature under a high vacuum. 1.4 g of colourless crystals which deliquesce in air are obtained.

IR (KBr): strong band at 660 cm$^{-1}$; further bands at 2980, 2920, 1460, 1100, 1060 and 880 cm$^{-1}$.

I.19. Preparation of hexa-(acetone)-iron(II) hexafluoroantimonate [process b)]

.5 g (3.94 mmol) of FeCl$_2$ (anhydrous) is dispersed in ml of acetone and the mixture is degassed under argon. 2.70 g (7.88 mmol) of solid AgSbF$_6$ are added. AgCl is formed in a slightly exothermic reaction. After 30 minutes, the AgCl is filtered off under an inert gas and washed with acetone. 1.1 g (7.72 mmol $\triangleq$ 98% of theory) AgCl result. The acetone solution is concentrated in vacuo and the product is crystallized with 30 ml of dry toluene. 2.35 g (7.68 mmol = 68% of theory) of white, very hygroscopic crystals are obtained.

$^1$H-NMR (D$_2$O): signal at 2.08 ppm singlet;

IR (KBr): strong band at 660 cm$^{-1}$; further bands at 1700, 1420, 1380, 1240 and 1050 cm$^{-1}$;

DSC: exothermic decomposition at 173° C.

I.20. Preparation of (acetone)-tin(II) hexafluoroantimonate [process b)]

Analogously to Example I.19, the above compound is isolated as a hygroscopic oil by reaction of stoichiometric amounts of SnCl$_2$ and 2AgSbF$_6$.

I.21. Preparation of (tetrahydrofuran)-tin(II) hexafluoroantimonate [process d)]

1.58 g (7.29 mmol) of SbF$_5$ are degassed with argon and cooled to $-78°$ C., and 5 ml of dry ethylene glycol dimethyl ether and 0.58 g (3.70 mmol) of SnF$_2$ are carefully added. The mixture is slowly warmed to room temperature. After about 2 hours, all the SnF$_2$ has dissolved. 20 ml of dry THF are added and the precipitate formed is rapidly filtered off under an inert gas, rinsed with THF and dried under a high vacuum at room temperature. 1.9 g of white, very hygroscopic crystals are obtained.

$^1$H-NMR ((D$_2$O): bands at 3.74 ppm (2H, multiplet), 1.87 ppm (2H, multiplet);

IR (KBr): strong band at 660 cm$^{-1}$; further bands at 3400, 2900, 2840, 1620, 1420, 1240, 1110 and 860 cm$^{-1}$.

I.22. Preparation of (tetrahydrofuran)-(diacetone alcohol)-iron(II) hexafluoroantimonate [process d)]

0.68 g (1.291 mmol) of Fe(SbF$_6$)$_2$ is added to 5 ml of acetone under argon. The iron salt dissolves in an exothermic reaction and a dark solution forms. After filtration to remove traces of insoluble product, THF is added and the precipitate formed is filtered off under an inert gas and washed three times with THF. Drying under a high vacuum at room temperature gives 0.9 g of yellowish hygroscopic crystals.

IR (KBr): strong band at 660 cm$^{-1}$, further bands at 3440, 3000, 2880, 1680, 1380, 1200, 1170, 1120 and 880 cm$^{-1}$;

$^1$H-NMR (D$_2$O): bands at 3.76 ppm (8H), 1.89 ppm (8H), 2.74 ppm (2H, singlet), 2.24 ppm (3H, singlet) and 1.27 ppm (6H, singlet), THF: diacetone alcohol=2:1.

I.23. Preparation of (polyethylene glycol)(acetone)-iron(II) hexafluoroantimonate [processes a)+e)]

2.5 g (3.25 mmol) of bis-($\eta^6$-mesitylene)-iron(II) hexafluoroantimonate are dissolved in 10 ml of acetone, and 0.7 g of polyethylene glycol 200 is added. After exposure analogously to Example I.2., the solution becomes completely bleached. After addition of toluene, the product is filtered off under an inert gas, washed and dried under a high vacuum. 2.5 g of a solid hygroscopic product results.

$^1$H-NMR (D$_2$O): bands at 3.93 ppm, 3.74 ppm and 2.23 ppm; acetone: polyethylene glycol about 1:1.

I.24. Preparation of (tetrahydrofuran)-aluminium(III) hexafluoroantimonate [process c)]

0.13 g (0.87 mmol) of aluminium trichloride is dissolved in 2 g of dry diethyl ether, and 5 ml of dry tetrahydrofuran are then added. 10 g (2.95 mmol) of solid triethyloxonium hexafluoroantimonate are added to the clear solution under argon as an inert gas and dissolve immediately. After 5 minutes, the product starts to crystallize out. After 2 hours at 40° C., the product is filtered off under an inert gas, washed twice with dry THF and dried at room temperature under a high vacuum. 0.9 g of fine colourless crystals is obtained.

$^1$H-NMR (D$_2$O): signals at 3.73 ppm (2H) and 1.78 ppm (2H);

IR (KBr): strong band at 660 cm$^{-1}$; further bands at 2880, 2900, 1450, 1360, 1250, 1220, 1150 and 880 cm$^{-1}$;

DSC: peak at 175° C.+220° C. (exothermic decomposition).

I.25. Preparation of (acetone)-magnesium(II) hexafluoroantimonate [process b)]

Analogously to Example I.19., the abovementioned compound is isolated as a very hygroscopic, colourless product by reaction of MgCl$_2$ and AgSbF$_6$.

I.26. Preparation of (acetic acid)-iron(II) hexafluoroantimonate [process a)]

3.0 g (3.91 mmol) of bis-($\eta^6$-mesitylene)-iron(II) hexafluoroantimonate are suspended in 25 ml of acetic acid and the suspension is degassed under argon. The suspension is heated to 120° C. After 1 hour, all the substances have dissolved and the red colour has disappeared. The acetic acid is concentrated and the product is concentrated to dryness under a high vacuum at room temperature. 3.05 g of solid, hygroscopic beige product are obtained.

$^1$H-NMR (D$_2$O): singlet at 2.09 ppm.

I.27. Preparation of (tetrahydrofuran)-iron(II) hexafluoroantimonate [process e)]

1.0 g of (acetic acid)-iron(II) hexafluoroantimonate are suspended in 10 ml of THF and the suspension is refluxed for 5 minutes. After cooling to room temperature, the product is filtered off under an inert gas and washed with THF. 0.95 g of white, very hygroscopic product results.

$^1$H-NMR (D$_2$O): bands at 3.75 ppm (2H) and 1.89 ppm (2H).

II. PREPARATION OF THE INITIATOR COMPOSITIONS ACCORDING TO THE INVENTION

Examples II.1. to II.3.

1 g of the complex according to Example I.9., I.4. or I.1. is dissolved, while heating (50° C./1 hour), in a solution consisting of 90 g of methylhexahydrophthalic anhydride and 10 g of a reaction product of two equivalents of tetrahydrophthalic anhydride and one equivalent of 2,2'-dimethylpropanediol.

Examples II.4. and II.5.

1 g of the complex according to Example I.1. or I.14 is dissolved in a solution consisting of 100 g of methylhexahydrophthalic anhydride while heating (50° C./1 hour).

Example II.6.

The 49.8% solution of the complex according to Example I.12. is diluted 100-fold with methylhexahydrophthalic anhydride.

Example II.7.

2 g of the complex according to Example I.9. are dissolved in 98 parts of diisocyanatodiphenylmethane, while heating (50° C./1 hour).

Example II.8.

2 g of the complex according to Example I.1. are dissolved in 98 parts of propylene carbonate.

Example II.9.

2 g of the complex according to Example I.1. are dissolved in 98 parts of caprolactone.

II.10. Preparation of an initiator solution containing (methylhexahydrophthalic anhydride)-tin(II)hexafluoroantimonate [process d)]

30 g of methylhexahydrophthalic anhydride are degassed at 120° C. under argon, and 1.02 g (6.50 mmol) of tin difluoride are added. The suspension is cooled in an ice bath and 2.80 g (12.92 mmol) of SbF$_5$ are slowly added in the course of 30 minutes. The mixture is warmed slowly to room temperature and stirred for 12 hours. During this procedure, the tin difluoride dissolves almost completely. The solution is then filtered over a G-4 filter frit. Virtually no residue remains. This initiator solution is diluted with methylhexahydrophthalic anhydride by a factor of 18.4.

II.11. Preparation of an initiator solution containing (methylhexahydrophthalic anhydride)-tin(II)hexafluoroantimonate fluoride [process d)]

Analogously to Example II.10., 3.70 g (2.36 mmol) of tin difluoride and 5.08 g (2.34 mmol) of SbF$_5$ are reacted in 32 g of methylhexahydrophthalic anhydride. After filtration to remove traces of insoluble product, the solution is diluted with methylhexahydrophthalic anhydride by a factor of 27.4.

II.12. Preparation of an initiator solution containing hexa-(methylhexahydrophthalic anhydride)-iron(II) hexafluoroantimonate [process d)]

3.8 g of methylhexahydrophthalic anhydride are degassed at 100° C. and kept under argon. 5.8 mg (0.11 mmol) of Fe(SbF$_6$)$_2$ are dissolved in this compound at 40° C. The Fe(SbF$_6$)$_2$ is prepared in accordance with the method of D. Gantar et al. J. Chem. Soc., Dalton Trans., 10, 2379-83 (1978) by reaction of FeF$_2$ and SbF$_5$ in HF. The solution is filtered and diluted 4.3-fold with methylhexahydrophthalic anhydride. A 1% solution of the abovementioned complex results.

III. USE EXAMPLES

Example III.1.

70 g of an industrial bisphenol A diglycidyl ether (epoxide value: 5.2 equivalents/kg), 30 g of 3,4-epoxycyclohexylmethyl 3',4'-epoxycyclohexanecarboxylate and 25 g of hardener components according to Examples II.1. to II.3. are mixed in an aluminium mould at room temperature and the mixture is then heated at 200° C. for 1 hour. Solid shaped articles having the following glass transition temperatures (measured by the DSC method) result:

T$_g$ using the initiator composition from Example II.1.: 181° C.;

T$_g$ using the initiator composition from Example II.2.: 181° C.;

T$_g$ using the initiator composition from Example II.3.: 179° C.

Example III.2.

100 g of an industrial bisphenol A diglycidyl ether (epoxide value: 5.2 equivalents/kg) and 25 g of hardener components according to Examples II.4. to II.5. are mixed in an aluminium mould at room temperature and the mixture is then heated at 200° C. for one hour. Solid shaped articles having the following glass transition temperatures (measured by the DSC method) result:

T$_g$ using the initiator composition from Example II.4.: 156° C.

T$_g$ using the initiator composition from Example II.5.: 154° C.;

T$_g$ using the initiator composition from Example II.6.: 164° C.;

Example III.3.

70 g of an industrial bisphenol A diglycidyl ether (epoxide value: 5.2 equivalents/kg), 30 g of 3,4-epoxycyclohexylmethyl 3',4'-epoxycyclohexanecarboxylate and 25 g of initiator component according to Examples II.7.-II.9. are mixed at room temperature and the mixture is then heated from 30° C. to 300° C. in a Mettler TA 3000 DSC apparatus. The heating-up rate is 10°

C./minute. The $T_g$ value is determined in the second DSC scan.

$T_g$ using the initiator composition from Example II.7.: 192° C.;

$T_g$ using the initiator composition from Example II.8.: 110° C.;

$T_g$ using the initiator composition from Example II.9.: 107° C.;

Example III.4.

A 1% solution of the particular complex in methylhexahydrophthalic anhydride is prepared, or an initiator solution according to Examples II.10.–II.12. is used. One part of these initiator compositions is mixed with 4 parts of a mixture of 70 g of an industrial bisphenol A diglycidyl ether (epoxide value 5.2 equivalents/kg) and 30 g of 3′,4′-epoxycyclohexylmethyl-3,4-epoxycyclohexanecarboxylate while cooling with ice. This reactive mixture is heated from 30° C. to 300° C. in a Mettler TA 3000 DSC apparatus with a heating-up rate of 10° C./minute. The $T_g$ value is then determined in a second DSC scan. The gel time of the reactive mixture is determined at 120° C. and at 80° C. on a hotplate. The results are listed in the following table.

TABLE 1

| Catalyst from Example | Gel time 120° | 80° C. | $T_g$ | Exothermicity maximum |
|---|---|---|---|---|
| I1 | 23″ | 47″ | 153° C. | 105° C. + 145° C. |
| I2 | 7″ | 27″ | 155° C. | 110° C. + 145° C. |
| I3 | 12″ | 35″ | 150° C. | 140° C. |
| I4 | 15″ | 43″ | 162° C. | 135° C. |
| I5 | 9″ | 35″ | 161° C. | 140° C. |
| I6 | 25″ | 50″ | 151° C. | 145° C. |
| I8 | 22″ | 50″ | 149° C. | 145° C. |
| I9 | 12″ | 29″ | 157° C. | 139° C. |
| I10 | 22″ | 48″ | 155° C. | 110° C. + 140° C. |
| I11 | 22″ | 50″ | 159° C. | 110° C. + 135° C. |
| I12 | 23″ | 48″ | 160° C. | 140° C. |
| I13 | 22″ | 45″ | 155° C. | 105° C. + 140° C. |
| I14 | 17″ | 43″ | 168° C. | 140° C. |
| I15 | 18″ | 45″ | 165° C. | 137° C. |
| I16 | 22″ | 55″ | 163° C. | 138° C. |
| I17 | 11″ | 30″ | 148° C. | 110° C. + 140° C. |
| I18 | 20″ | 80″ | 163° C. | 135° C. |
| I19 | 10″ | 37″ | 150° C. | 145° C. |
| I20 | 17″ | 47″ | 166° C. | 142° C. |
| I21 | 12″ | 65″ | 152° C. | 150° C. |
| I11 | 15″ | 95″ | 152° C. | 108° C. + 145° C. |
| I110 | 15″ | 75″ | 154° C. | 110° C. + 148° C. |
| I112 | 24″ | 120″ | 152° C. | 110° C. + 150° C. |
| I22 | 23″ | 90″ | 157° C. | 110° C. + 150° C. |
| I23 | 12″ | 35″ | 158° C. | 100° C. + 145° C. |
| I24 (0.5% complex) | 20″ | 90″ | 158° C. | 180° C. |
| I25 | 12″ | 50″ | 154° C. | 142° C. |
| I26 | 14″ | 55″ | 157° C. | 100° C. + 150° C. |

What is claimed is:

1. A composition comprising
   i) an anhydride of a polycarboxylic acid, a polyisocyanate, a cyclic carbonate, a lactone or a mixture thereof, and dissolved therein
   ii) at least one compound of the formula I $$[M^{+n}(L)_x]^{n+}nX^- \qquad (I)$$

in which n is 2 or 3, M is a metal cation selected from the group consisting of $Zn^{2+}$, $Mg^{2+}$, $Fe^{2+}$, $Co^{2+}$, $Ni^{2+}$, $Cr^{2+}$, $Ru^{2+}$, $Mn^{2+}$, $Sn^{2+}$, $VO^{2+}$, $Fe^{3+}$, $Al^{3+}$ and $Co^{3+}$, X is an anion which is selected from the group consisting of $AsF_6^-$, $SbF_6^-$, $BiF_6^-$ and derivatives derived from these anions in which some of the fluorine atoms are replaced by hydroxyl groups, or in which up to 50% of the anions $X^-$, based on the total amount of anions, can also be any desired anions, L is water or an organic $\sigma$-donor ligand which contains, as ligand sites, one or more functional radicals selected from the group consisting of —CO—, —CO—O—, —O—CO—O— and —O—, and which forms $\sigma$-bonds with the central atom via the oxygen or via the oxygen atoms, and x is an integer from 0 to 6, it being possible for the ligands L to differ within the context of the definitions given.

2. A composition according to claim 1, in which L is selected from the group consisting of water, ethers, ketones, carboxylic acid anhydrides, carboxylic acid esters and the lactones of dicarboxylic acids.

3. A composition according to claim 1, in which component ii) is a compound of the formula II $$[(L^1)_a M^{+n} (L^2)_b]^{n+} nX^- \qquad (II)$$

in which M, X and n are as defined in claim 1, $L^1$ is a mono- to hexadentate $\sigma$-donor ligand and is an aliphatic, cycloaliphatic, aromatic or araliphatic compound having one or two ketone, anhydride, carbonate or ester groups or one to six ether groups per molecule, it being possible for the ligands $L^1$ of a compound of the formula II to differ in the context of the definitions given, $L^2$ is water, b is an integer from 0 to 2, and, if $L^1$ is a monodentate ligand, a is an integer from 4 to 6 and the sum of a and b is in each case 6, and if $L^1$ is a bidentate ligand, a is an integer from 2 to 3 and the sum of 2a and b is in each case 6, and if $L^1$ is a tridentate ligand, a is 1 or 2 and the sum of 3a and b is 6, and if $L^1$ is a tetra-, penta- or hexadentate ligand, a is 1 and the sum of 4a and b or of 5a and b or of 6a and b is 6 or 8.

4. A composition according to claim 1, in which component i) is a polyisocyanate or an anhydride of a polycarboxylic acid.

5. A composition according to claim 1, in which the amount of component ii) is between 0.05 and 10% by weight, based on the total weight of components i) and ii).

6. A composition according to claim 3, in which n is 2, b is 0 and a is 6 or 3.

7. A composition according to claim 1, which is liquid below 50° C.

8. A process for the preparation of the composition according to claim 1, which comprises dissolving at least one compound of the formula I according to claim 1 in a component i) according to claim 1.

9. A composition according to claim 1 wherein M is selected from the group consisting of $Zn^{2+}$, $Mg^{2+}$, $Sn^{2+}$, $Al^{3+}$ and $Fe^{2+}$.

10. A composition according to claim 3 wherein M is selected from the group consisting of $Zn^{2+}$, $Mg^{2+}$, $Sn^{2+}$, $Al^{3+}$ and $Fe^{2+}$.

11. A composition according to claim 1 wherein $X^-$ is $AsF_6^-$, $SbF_5(OH)^-$, $BiF_6^-$, or $SbF_6^-$.

12. A composition according to claim 3 wherein $X^-$ is $AsF_6^-$, $SbF_5(OH)^-$, $BiF_6^-$, or $SbF_6^-$.

* * * * *